(12) United States Patent
Pusiol et al.

(10) Patent No.: US 7,872,474 B2
(45) Date of Patent: Jan. 18, 2011

(54) MAGNETIC RESONANCE BASED APPARATUS AND METHOD TO ANALYZE AND TO MEASURE THE BI-DIRECTIONAL FLOW REGIME IN A TRANSPORT OR A PRODUCTION CONDUIT OF COMPLEX FLUIDS, IN REAL TIME AND REAL FLOW-RATE

(75) Inventors: Daniel Pusiol, Cordoba (AR); Mariela Carpinella, Cordoba (AR); Gabriela Albert, Cordoba (AR); Tristan Osan, Cordoba (AR); Juan Manuel Olle, Cordoba (AR); John Justin Freeman, Brookshire, TX (US); Matthias Appel, Houston, TX (US); Irene Silvina Lopez Gamundi Espejo, Bellaire, TX (US)

(73) Assignee: Shell Oil Company, Houston, TX (US)

( * ) Notice: Subject to any disclaimer, the term of this patent is extended or adjusted under 35 U.S.C. 154(b) by 288 days.

(21) Appl. No.: 11/945,880

(22) Filed: Nov. 27, 2007

(65) Prior Publication Data

US 2008/0174309 A1 Jul. 24, 2008

Related U.S. Application Data

(60) Provisional application No. 60/861,668, filed on Nov. 29, 2006.

(51) Int. Cl.
*G01V 3/00* (2006.01)
(52) U.S. Cl. .................................. 324/306; 324/303
(58) Field of Classification Search ................ 324/303, 324/306
See application file for complete search history.

(56) References Cited

U.S. PATENT DOCUMENTS

| | | | |
|---|---|---|---|
| 4,785,245 | A | 11/1988 | Lew et al. |
| 5,684,399 | A * | 11/1997 | Bayer ......................... 324/306 |
| 6,046,587 | A | 4/2000 | King et al. |
| 6,111,408 | A | 8/2000 | Blades et al. |
| 6,268,727 | B1 | 7/2001 | King et al. |
| 6,452,390 | B1 | 9/2002 | Wollin |
| 6,577,125 | B2 | 6/2003 | Prammer et al. |
| 6,737,864 | B2 | 5/2004 | Prammer et al. |
| 6,825,657 | B2 | 11/2004 | Kleinberg et al. |
| 6,891,369 | B2 | 5/2005 | Hurlimann et al. |
| 7,501,819 | B2 * | 3/2009 | Ong ........................... 324/306 |
| 2003/0210050 | A1 | 11/2003 | Prammer et al. |
| 2004/0015332 | A1 | 1/2004 | Martin et al. |
| 2005/0040822 | A1 | 2/2005 | Heaton |

(Continued)

OTHER PUBLICATIONS

K. Halbach "Design Of Permanent Multipole Magnets With Oriented Rare Earth Cobalt Material" Nucl. Instr. Meth, 169, pp. 1-10 (1980).

(Continued)

*Primary Examiner*—Louis M Arana

(57) ABSTRACT

An apparatus and a method is provided based on the Magnetic Resonance techniques to analyze and measure a uni- and/or a bi-directional flow regime of multiphase fluids in a transport and production conduct, in real time and flow-rates, based on a magnetic resonance analytical module, two magnetic pre-polarization modules of variable effective length and a control computer of data acquisition and transfer, all associated to each other.

12 Claims, 9 Drawing Sheets

U.S. PATENT DOCUMENTS

2006/0020403 A1 1/2006 Pusiol
2006/0122779 A1 6/2006 Minh et al.

OTHER PUBLICATIONS

Klaus Halbach "Strong Rare Earth Quadrupoles" IEEE Trans. Nucl. Sci., vol. NS-26, No. 3, Jun. 1979.

H. Raich; P. Blümler "Design and Construction of a Dipolar Halbach Array with a Homogeneous Field from Identical Bar Magnets; NMR Mandhalas" Concpets Magn. Reson. Part B (Magn Reson Eng), 23B, 16 (2004).

"MRI Halbach 0.23 T magnet" Magneticasoft Nice, France http://www.magneticasoft.com.

* cited by examiner

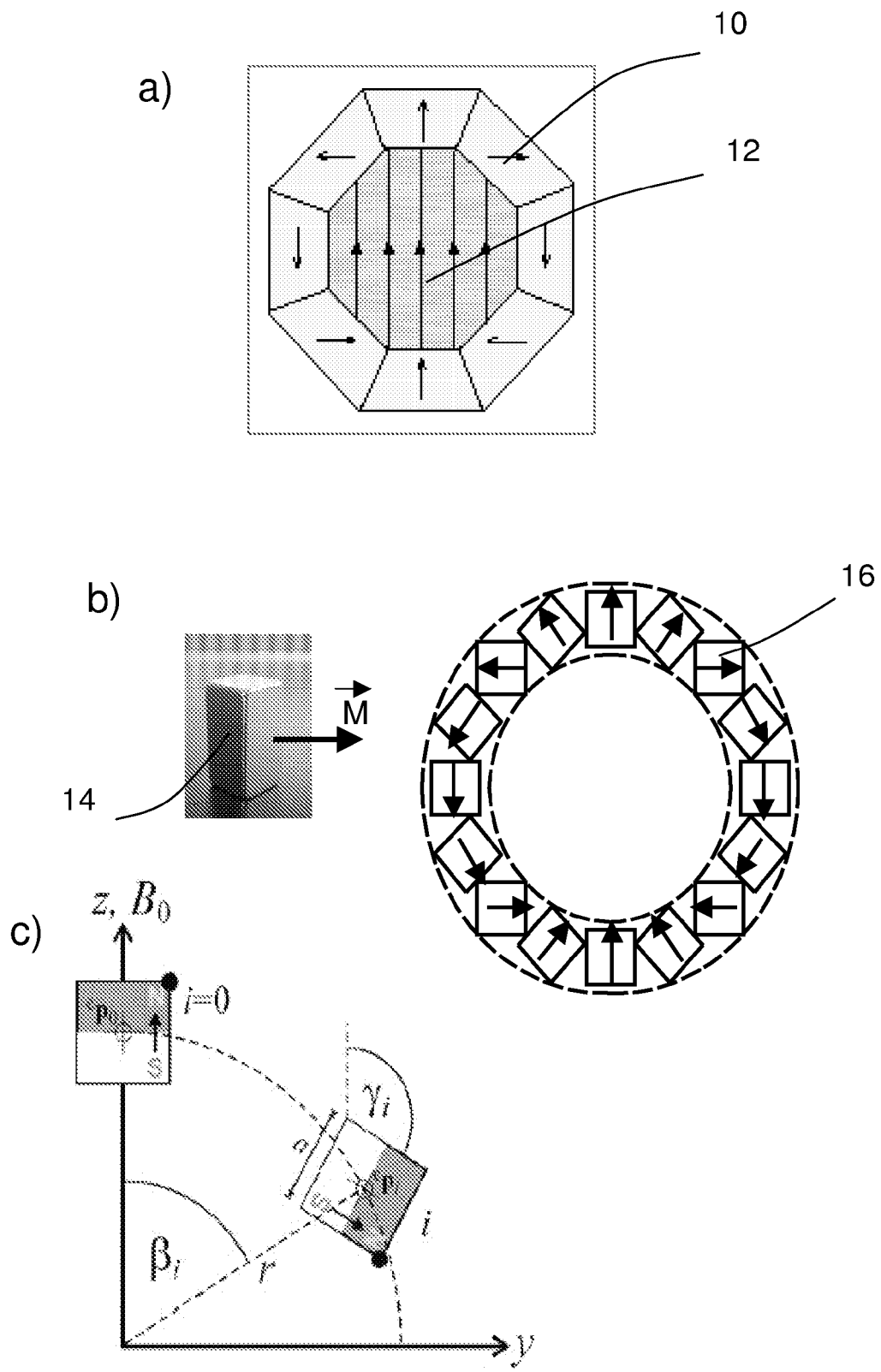
Figure 3: Previous Art

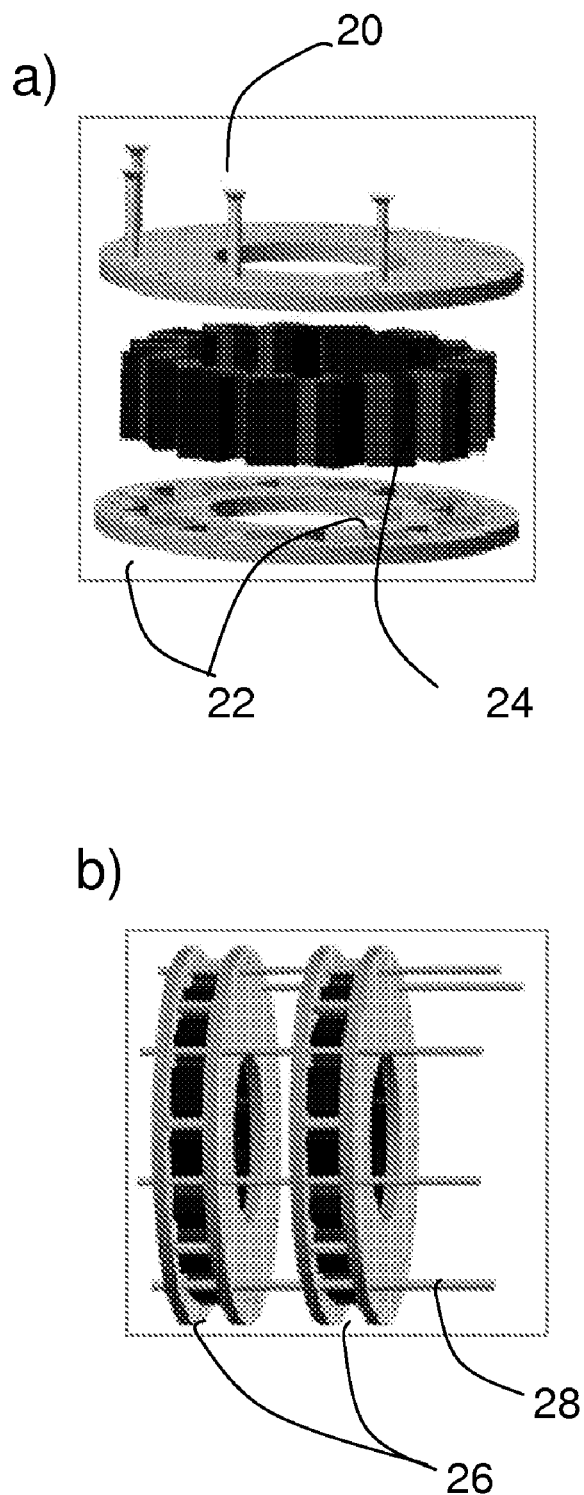
Figure 4: Previous Art a)
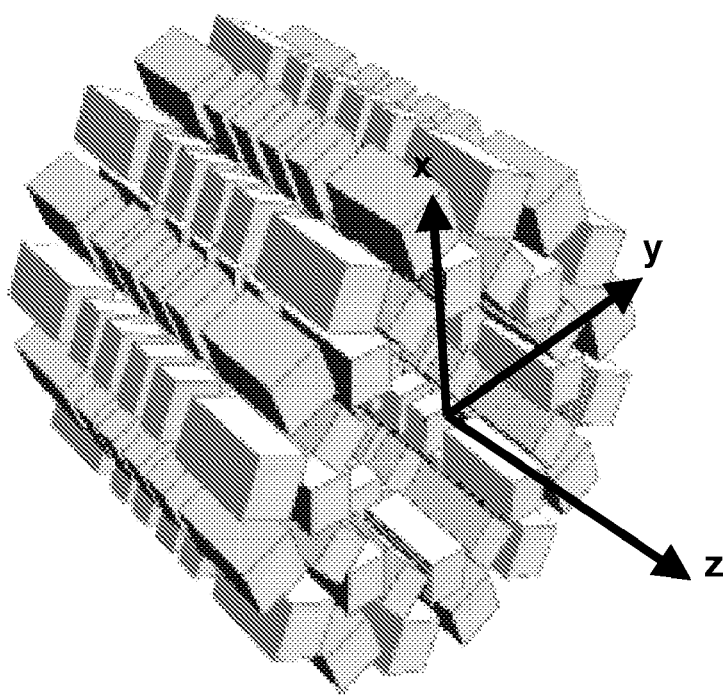
b)
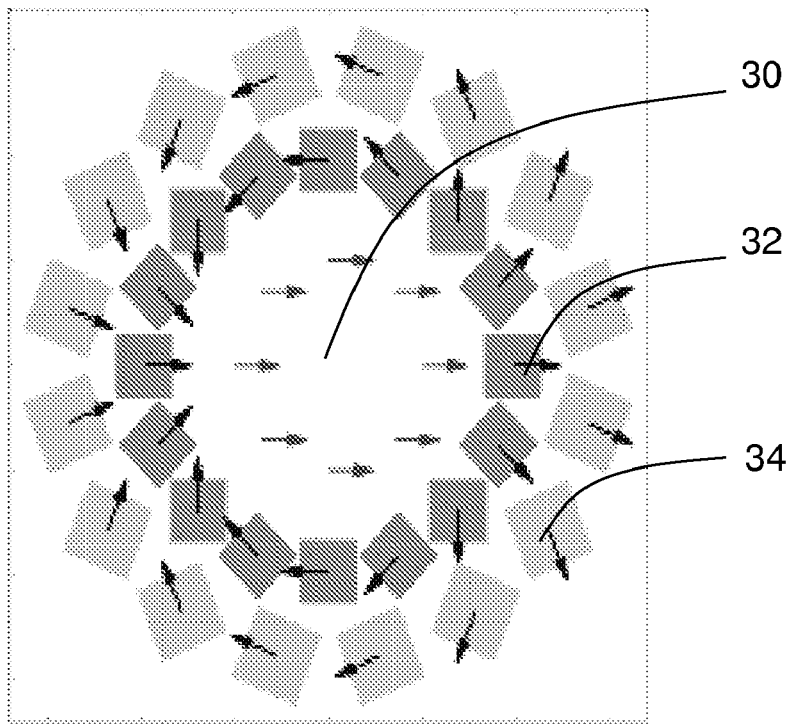
Figure 5: Previous Art

MAGNETIC RESONANCE BASED APPARATUS AND METHOD TO ANALYZE AND TO MEASURE THE BI-DIRECTIONAL FLOW REGIME IN A TRANSPORT OR A PRODUCTION CONDUIT OF COMPLEX FLUIDS, IN REAL TIME AND REAL FLOW-RATE

FIELD OF THE INVENTION

The present invention is related to the direct determination in the production line, of the flow regime in a multiphase complex fluid, by the selective measurement by Magnetic Resonance (MR) of the velocity profile of each separate phase, in a transversal slice to the flow direction. The present invention is specifically related to a method and an apparatus to measure, in real time and real production volumes, the individual component flow-rates, the relative proportions of the different phases that compose the complex fluid and the spatial profile of velocities in the fluid vein, in both uni and bidirectional flowing fluids. In particular, the present invention is applied preferably to the analysis of the flow in oil industry production veins, as well as in other conducts that transport diverse types of fluids, including, for example, the cases where water and petroleum move in opposite directions. The analysis is performed on a non-invasive and non-destructive way and independently from the state of the mixture, this means for example, if it is composed by petroleum, water and gas in separated phases or in a phase in emulsion.

Other applications in the mining, food, chemical, pharmaceutical industry, etc., are also possible, being for instance one fluid composed of miscible and/or non-miscible pastes, or mixtures of liquids that have solids in suspension.

BACKGROUND OF THE INVENTION

Many solutions exist in the literature using Magnetic Resonance techniques to analyze directly on the liquid pipe and in real time, different properties of the transport and/or production of fluids. We can for instance mention:

1. Up from the measurement of the relaxation times $T_1$ and $T_2$ and from the coefficient of Molecular diffusion D, the petrophysical properties of the extraction fluid are measured in real time and in the real conditions of reservoir, including:
   a. the level of contamination of the fluid due to, by example, filtrations of water, mud, etc.;
   b. viscosity and the relation water/gas/petroleum.

These measurements are made in surface as well as in the pit (continental or offshore) and eliminate ambiguities associated with samples extraction as well as the corresponding transport procedures. Some analytical methods based on the Magnetic Resonance and its associated devices are described, for example, in the U.S. Pat. No. 6,111,408, "Nuclear Magnetic Resonance Sensing Apparatus and for Techniques down hole Measurements", by T. Blades et al.; U.S. Pat. No. 6,737,864 B2, "Magnetic Resonance Fluid Analysis and Method", by M. G. Prammer et al.; U.S. Pat. No. 6,825,657 B2, "Magnetic Resonance for Method Characterizing Fluid Samples Withdrawn from Subsubsurface Earth Formations", by R. L. Kleinberg et al.; U.S. Pat. No. 6,891,369 B2, "Magnetic Resonance Method and Logging for Apparatus Fluid Analysis", by M. D. Hurlimann; U.S. 2005/0040822 A1 "Multimeasurements NMR Analysis based on Maximum Entropy", by N. Heaton and 2006/0122779 U.S.A1 "Interpretation for Methods NMR Diffussion-T2 Maps" by Chang Cao Ming and N. Heaton and the therein contained references.

2. Another group of tools, also based on the Magnetic Resonance technique, has been divulgated, to determine the cut (or proportion of petroleum and water) and the flow in the fluid vein. On the one hand, the determination of petroleum and water cut is generally is carried on by the Magnetic Resonance signal weighted by the individual spin-lattice relaxation times $T_1$ of the fluid. In particular, for the case of a mixture of petroleum and water, water T1 differs from those of petroleum. Moreover, it is also possible to measure the cut of the light and heavy elements of petroleum, since its $T_1$ values differ enough to isolate the different MR signals. See by example the U.S. Pat. No. 4,785,245. On the other hand, for the flow-rate measurement, three different basic principles can be grouped:

The measurement of the fluid flow-rate through the measurement of the "flight time" of the fluid between two Magnetic Resonance spectrometers: (or between two sensors of a same spectrometer). See the U.S. Pat. No. 6,046,587 "Measurements of Flow Fractions, Flow Velocities and Flow Rates of a Multiphase Fluid using NMR Sensing" and the U.S. Pat. No. 6,268,727 "Measurements of Flow Fractions, Flow Velocities and Flow Rates of a Multiphase Fluid using ESR Sensing", by J. D. King, Q. Nor and A. De los Santos, which disclose a sensor that uses at least two MR spectrometers or one MR and another Electron Paramagnetic Resonance one. The basic principle of the measurement methodology is based on what is known as the "flight or passage time" of MR-excited fluid nuclei between both MR spectrometers. Another variant is the US Patent Application No. 2004/001532, by M. Ramia, D. J. Pusiol, C. A. Martin, E. Fried and R. Garnero, "Method and procedure to measure fluid flow and fluid fraction, and equipment used to that end". In this case there is only one electronic part, shared by two sensorial coils, being the operation principle the same as the one described before; namely, the speed of the flow through flight time of the water and petroleum molecules in the space between both sensorial coils is separately measured. Those are little practical and expensive to be implemented, as well as of difficult application in petroleum fields with rigorous climatic conditions generally.

Another methodology is based on the spatial encoding of the flow velocity by a magnetic field gradient in the direction of the flow. The gradients (static and/or electronically pulsed) are employed to modulate the protons spin precession phase. It means that the spatial codification is made in what it is known as the Laboratory Frame. The flow meter with fluid phase separation that uses the pulsed electromagnetic field gradient is disclosed, for instance, by the U.S. Pat. No. 6,452,390, by E. Wollin, "Magnetic Resonance Analyzing Flow Meter and Flow Measuring Method". This method has the disadvantage that, at the speeds at which the protons commonly move in the magnetic field when the fluid flow-rate is measured under reservoir conditions, is too fast. Therefore, the application of fast rise time magnetic field gradients switching on and off is of difficult technological implementation. This means that this methodology is generally restricted to measurements at relatively low flow-rates. Another variant which avoids high electric currents by including a permanent longitudinal gradient field is described in the US Patent Application No. US 2006/0020403, by D. J. Pusiol "Device and Method for real time direct measurement of the Flow-Rate of a Multi-Component Complex Fluid". This invent divulgates a flow meter and a cut sensor constituted by only one coil associated to a magnet of slightly oblique flat polar faces. The device generates a constant magnetic field, in addition with a magnetic field gradient in the direction of the flow. The spatial codification of the temporal position of the resonant nuclei is done by a linear magnetic field gradient in the volume that occupies the excitation/detection Magnetic Resonance coil. For high flow speeds, this gradient must be increased to reach the necessary effectiveness in the space codification process of the protons that compose the circulating complex fluid. But the increment of the magnetic field gradient strength implies a broadening in the MR line width. Therefore, the MR signal to noise ratio deteriorates. The maximum limit of the flow that is possible to be measured by the mentioned invention is determined by the maximum value of the magnetic field gradient that is possible to apply to the fluid, before the signal is deteriorated so that the required precision is not anymore reached for this particular use.

All the above described solutions measure only the average of flow-rates of the fluid components, but to evaluate the efficiency of the methods of extraction, pumping, transport, water injection in secondary extraction, etc., it is necessary to be able to evaluate, in the line and in reservoir conditions, the flow regime of the fluid. Therefore, it is also necessary to know the velocity profile of each individual component of the fluid in spatially selected volume elements.

SUMMARY

The above drawbacks and difficulties are solved by this invention, as the invented method and device allow real time measurement of the profile of the flow-rate and proportions of the different components conforming a multicomponent complex fluid in a non-invasive and non-destructive way, i.e. for example, regardless of the fact of it being formed by oil and water in separate phases or as an emulsion.

It is to borne in mind that this invention can also be applied to other technological fields such as, for example, that of the dairy industry, for determination of the milk-yogurt ratio, food and extruded organic materials, etc.

More specifically, this invention is related to a method and device for a Magnetic Resonance based apparatus and method to analyze and to measure a bi-directional flow regime in a transport or production pipe of complex fluids, in real time and flow.

The analytical magnetic resonance based method to be applied in the oil industry is the following one:

The circulating fluid comes into a region of pre-polarization to codify the component or phase whose relative proportion in the fluid and velocity profile is to be measured or analyzed. For that purpose we use the properties of longitudinal relaxation—characterized by T1—of each component of the fluid, the media speed of the fluid and the length of such magnetic field.

Secondly, the properly polarized spins come into a region in which a transversal (and if not, a longitudinal) magnetic field has been generated, which also has a field gradient—properly designed according to the symmetry of the velocity profile to be measured—that can be reoriented in order to obtain different projections of the spins density of the previously selected components and their relative speed.

Thirdly, an adequate excitation/detection pulse sequence measures and characterizes the flow regime by the following sequence:

The spatial selection of a volume element located inside the exciting coil is made by a resonant radiofrequency soft pulse.

Once the volume element to be measured is selected, the average speed of the previously selected component in the prepolarization step, contained in such selected volume element, is measured. The slope of the echoes linear decay characterizes the volume element velocity of the selected fluid component. Such lineal decay in the spin echo signal of both the volume and the selected fluid component refers essentially to the portion of said volume element that stays in the volume of the exciting-receiving coil. In the temporary ends of said decay dominate the relaxation processes, and as such, this is characterized by an exponential component in the temporal evolution of the spin echo intensity.

For each excitation frequency, or volume of selected fluid, steps a and b are repeated till obtaining a matrix whose elements represent the speed and respective proportions in different spatial positions, preferably in the transversal slice of the fluid direction.

Finally, the previous steps are repeated for:

Different magnetic field gradient directions and/or intensities (spatial codification).

Different effective lengths of the prepolarization field.

Different polarization fields (right or left) in order to make a bi-directional fluid flow characterization.

The apparatus invented here to analyze and to measure the uni and bidirectional flow regime is a measurement and analysis module of magnetic resonance, two magnetic prepolarization modules of variable effective length and a control computer of acquisition and data transfer, all associated to each other. The measurement and analysis MR module is disposed symmetrically left and right with the two prepolarization modules. The fluid conduct passes through that modules array.

The magnetic resonance analytical module generates a homogeneous, thermally compensated and constant magnetic field, with addition of a space location gradient, constituted by a plurality of magnetic bars of different sizes and materials, that constitute a plurality of discs of variable thicknesses, piled up and associated among themselves.

The protons prepolarization magnetic field modules of variable effective length consists of successive discrete Halbach-type cylindrical segments, that can be piled and associated to each other to select the components of the fluid with successive minor spin-lattice relaxation times.

BRIEF DESCRIPTION OF THE DRAWINGS

The invention shall be best understood when read in conjunction with the following figures:

FIGS. 3a)-3c): Illustrate the previous art for a magnet of the Halbach type with disc form, constructed with properly located discrete cross-section rectangular magnetic bars.

FIG. 4: a) Illustrates a way to arrange the bars as described in FIG. 3; b) illustrates a convenient way to pile up those discs shown above.

FIGS. 5a) and 5b): Illustrate an embodiment of the previous art for the homogenization of the internal magnetic field of the Halbach cylinder, which is commercially applied in Magnetic Resonance Imaging applications.

DETAILED DESCRIPTION OF THE PREFERRED EMBODIMENTS

Figure 1:
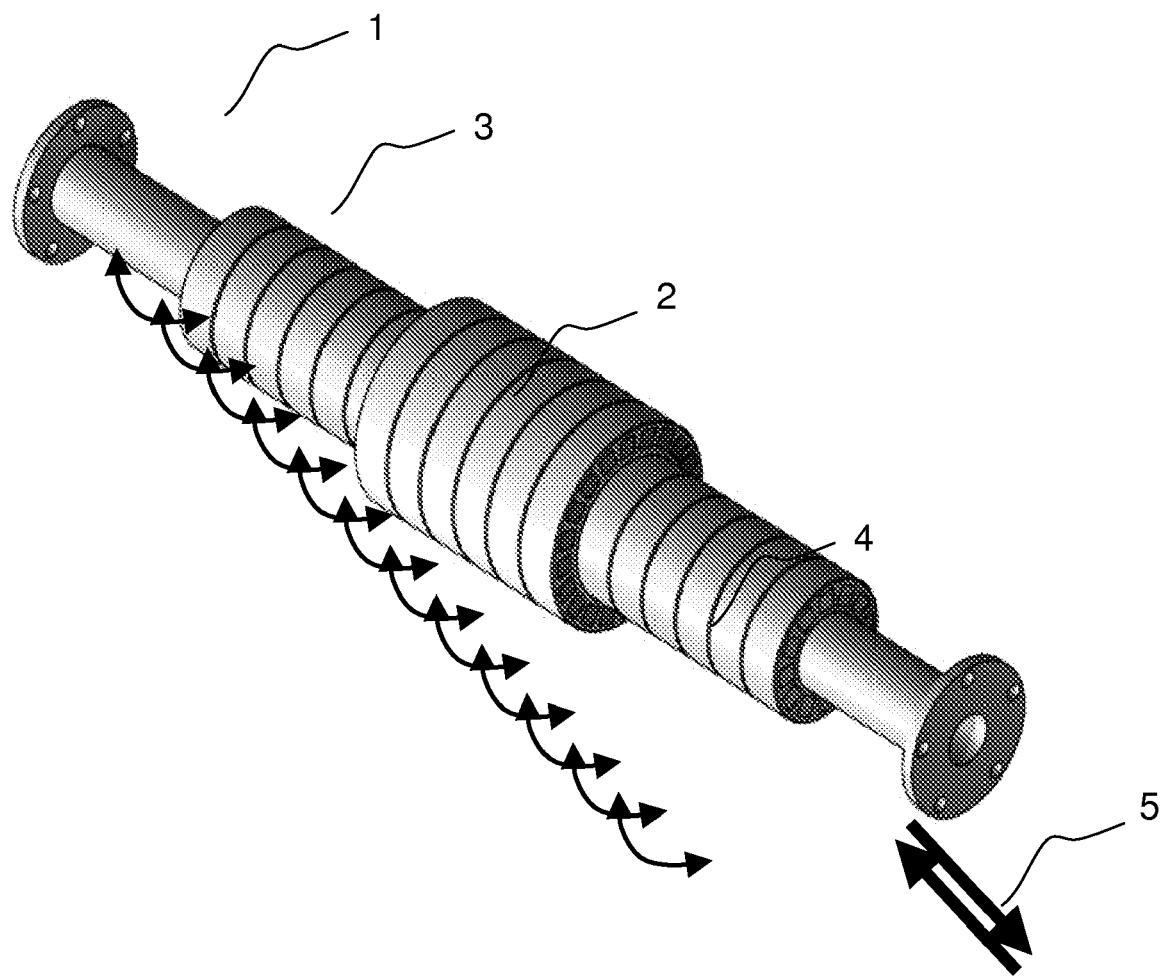
FIG. 1: Illustrates a simplified block diagram of the preferred embodiment of the present invention.

FIG. 1 shows a simplified block chart of the preferred embodiment of this invention. The complex fluid flows through the production vein 1 in any of the two possible directions; a phase can also flow in one direction and the other/others in the opposite one 5. If the flow of the phase, whose regime needs to be measured or characterized, flows from the left to the right, for example, it comes first into the prepolarization magnet of effective variable length to polarize the spins of the phases that come from the left 3; then the fluid comes into the measurement and characterization set of the velocity profile 2. The following step 4 produces no effects in this situation, as it is adjusted to an effective zero polarization length. The magnetic field generated in the first step 3 allows choosing the phase of the fluid to be measured in the following step 2. This operation is made by the relation between the average velocity of such phase in the pipe, the value of the relaxation time T1, and the effective length that the fluid flows in such prepolarization magnetic field. For fluids with more than two phases, this procedure is repeated as many times as necessary, each time with different effective prepolarization lengths. We will further return to the detailed description of this point. Once the cut is codified as explained before, the fluid comes in the set of local measurement of the velocity profile 2. In a preferred embodiment, this stage consists of a magnet that generates a magnetic field in a transversal direction to the flow, able to be used in experiments of magnetic resonance, which have also a magnetic field gradient in a Cartesian direction for a preferred application, or in a polar (or radial) direction for another preferred application. Such Cartesian direction may be oriented by the rotation of the measurement device, or by the disposition of many electromagnets arranged in a convenient way. Inside the magnet are the radiofrequency coils used to excite the nuclei of the prepolarized phases in step 3, and to receive the magnetic resonance signal. The sequence of events is the following:

First, all the nuclei that are in a desired portion of the total volume contained in the radiofrequency coil are excited. This volume is determined by a first radiofrequency pulse, with pure spectral characteristic, or narrow band, also known as "soft pulse".

Immediately, a sequence that reads the quantity of the previously selected spins still remaining in the volume of the detection coil starts. Such reading is preferably made by a sequence of refocalization pulses of the magnetization and also by the measurement of the generated spin eco intensity. Said refocalization pulses may be narrow range pulses (soft pulses), or wide range pulses (hard pulses). A preferred sequence of pulses is known as spatially selective CPMG (see for example, R. Kimmich, "*NMR-Tomography, Diffusometry, Relaxometry*", Springer-Verlag, Berlin-Heildelberg (1997)). As it later will be described, in a range of intervals between the reading pulses, there is a lineal relation in the signal intensity decay of the spin eco. This invention also proves that the slope of such lineal relation is proportional to the fluid local velocity. This process is repeated for several frequencies of the spatial selection pulse and several orientations of the magnetic field gradient with respect to a singularity in the symmetry of the transversal velocity profile of the fluid.

If necessary, other magnetic field gradient in the fluid direction can be added in order to allow the selection a thick slice of the total transversal volume contained in the radiofrequency coil.

Figure 2:
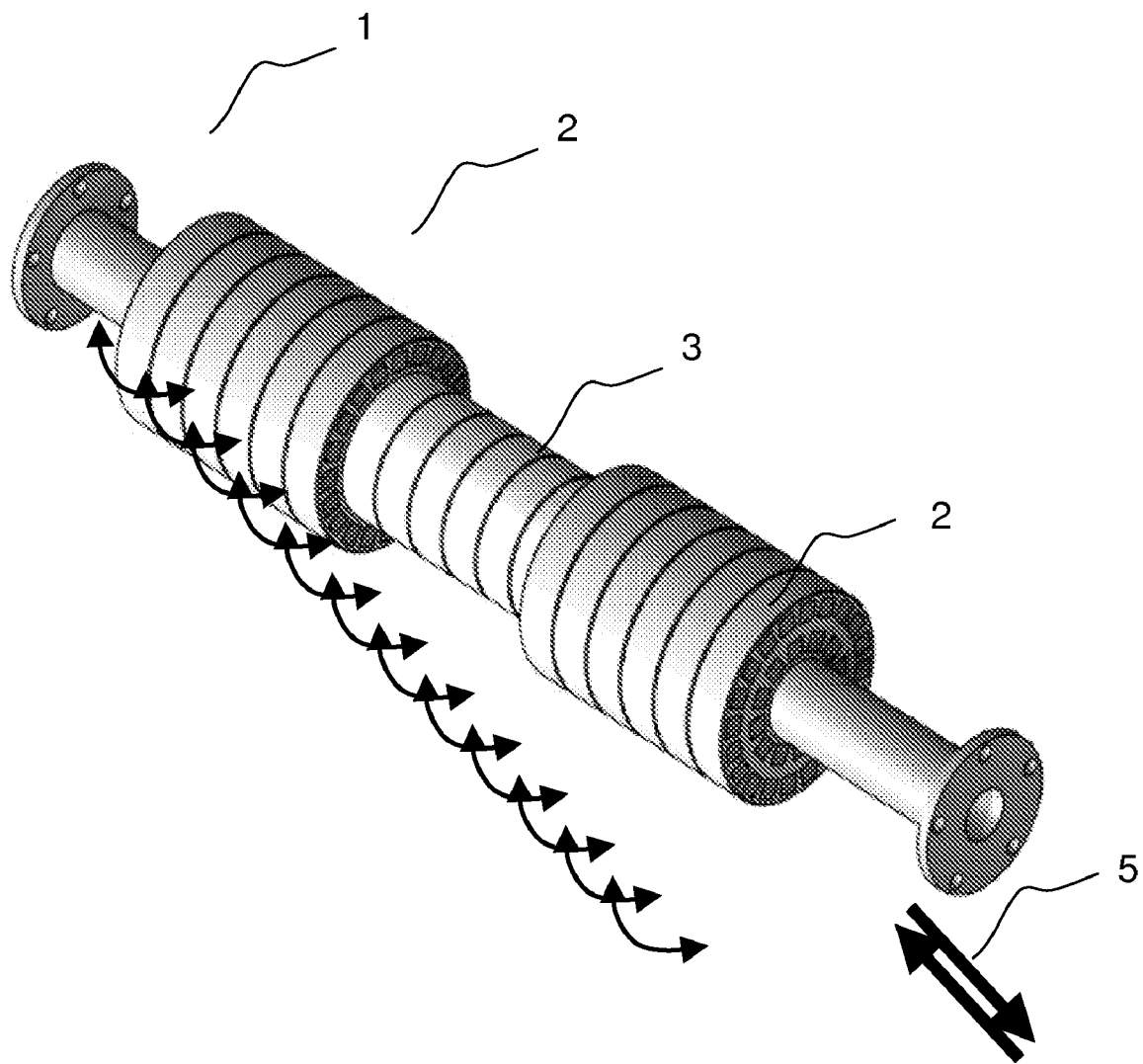
FIG. 2: Illustrates another preferred embodiment, as it has been formed with two measurement and characterization of the velocity profile devices in the extremities of a sole prepolarization region of variable effective length.

FIG. 2 shows another preferred embodiment. It is composed of two analysis modules of the flow regime (one for each direction of the fluid) located at both lateral ends; and in the center we reach a sole section of prepolarization. In this way, with two spectrometers we can measure simultaneously both fluid directions. Further we will describe in detail each one of the parts and/or devices of the preferred process and the preferred set. To do that we revise a part of the previous art, especially that concerning magnets.

There exist in the previous art preferably cylindrical permanent magnets with tubular geometry, based on polarized rare earth alloy segments. The most known and commercially available are the so called "magical cylinders", standing out among them the Halbach magnets. The idea of Halbach was to use polarized segments, to form the cylinder or ring, in such a way that their magnetizations should fulfill the theoretical requirements for the angle ($\gamma_i=(1+k_i)\beta_i$) (See, K. Halbach, "*Design of permanent multipole magnets with oriented rare earth cobalt materials*". Nucl. Instr. Meth., 169, 1 (1980); and K. Halbach, "*Strong rare earth cobalt quadrupoles*". IEEE Trans. Nucl. Sci. 26, 3882 (1079)). In the FIG. 3a) a previous art magical Halbach cylinder composed by 8 segments of trapezoidal shape 10, which generate in the inner volume a sufficiently homogenous cross magnetic field 12 for uses in Magnetic Resonance experiments. This type of magnets have been improved, including a configuration to compensate thermal changes in the magnetic field (to see for example, M. G. Prammer and P. Masak, "Temperature compensated magnetic circuit". Patent Application Publication U.S. 2003/0210050 and Ms. G. Prammer and P. Masak, "Temperature compensated magnetic field apparatus for NMR measurements" U.S. Pat. No. 6,577,125 B2). In a recent work H. Raich and B. Blümber, "*Design and construction of to Dipole Halbach Array with to Homogeneous Field from identical Bar Magnets: NMR Mandhalas*". Concepts Magn. Reson. Part B (Magn Reson Eng), 23B, 16 (2004) propose, as shown in FIG. 3b), to use conventional magnetic bars 14, adequately arranged and oriented 16 in order to obtain a transversally oriented magnetic field. By this design, the authors obtain a magnet of relatively small weight than that of a conventional Halbach, although with smaller homogeneity in the useful space. FIG. 3c) illustrates the relative angles between the bars to obtain the most homogenous possible internal field, in accordance to the equation:

$$\gamma_i=(1+p)\beta_i$$

FIG. 4 illustrates a previous art embodiment proposed by Raich and Blümber. A plurality of rectangular magnetic bars 20 are arranged together with two discs of non-magnetic material 22, fixed by the screws 24 also of non-magnetic material. These discs 26 are piled up and held by non-magnetic screws 28, as illustrated in FIG. 4b), to form a cylindrical permanent magnet. Before using Magnetic Resonance applications, it is necessary to homogenize and thermally compensate the magnetic field in the inner region of that cylindrical device.

FIG. 5 illustrates an embodiment of the previous art (see MAGNETICASOFT, Nice, France, "MRI Halbach 0.23 T magnet", available in http://www.maxneticasoft.com/ of a magnet designed to be used in images devices by Magnetic Resonance (MRI). The useful space for images by Magnetic Resonance 30 is surrounded by two concentric cylinders. The inner cylinder 32 generates the main component of the field and the outer cylinder 34 is slightly rotated with respect to the first one and serves on one hand to increase the magnetic field in the zone 30, and on the other hand to homogenize the magnetic field.

Figure 6:
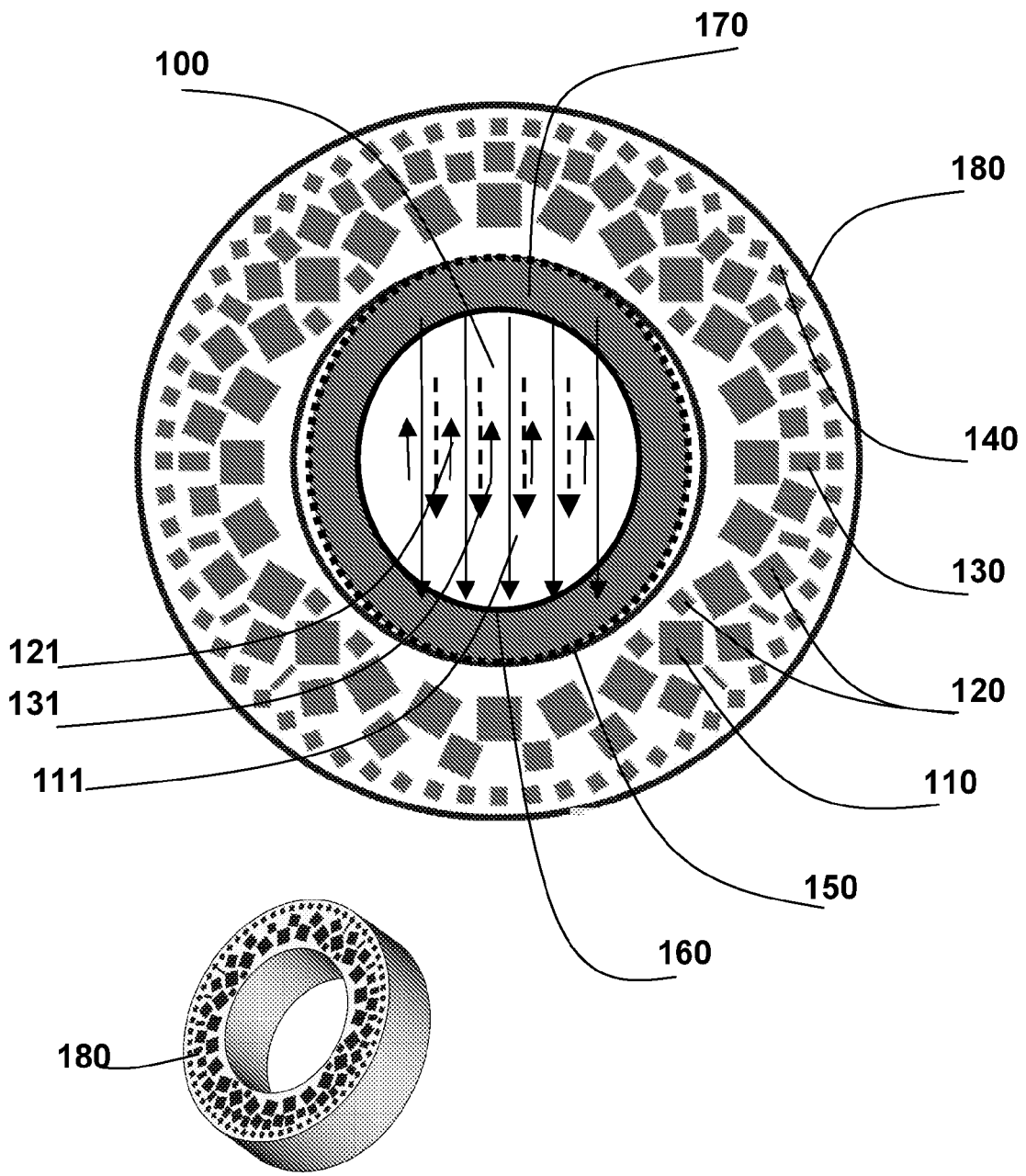
FIG. 6: Illustrates the preferred embodiment for a measurement and characterization set of the velocity profile constituted by an adjustment of magnetic bars that compose the permanent magnet of the sensorial element, which has "Shimming" temperature compensation, and gradient generation in the x direction.

FIG. 6 illustrates a preferred embodiment for a set of measurement and characterization of the velocity profile. This device is constituted by an array of magnetic bars which compose the permanent magnet of the magnetic resonance analysis device. The rectangular bars array is designed to compensate thermal changes in the magnetization, inner magnetic field shimming, and the magnetic field gradient generation. Such bars array form discs of variable thickness with the following properties:

In the zone of interest 100 (delimited by the dotted circle in FIG. 6) a magnetic field Bx 111 is produced and a gradient of transversal magnetic field Gx 131 superposed to Bx, both having the following properties and characteristics:

Gx is transversal to the flow direction.

Bx is sufficiently homogenous and thermally stabilized for Magnetic Resonance experiments.

This field is generated by a plurality of magnetized bars 110, 120, 130 and 140, which are properly arranged to produce respectively the magnetic field Bx 111, the homogenization effect or magnetic field shimming, the Gx Gradient generation 131 and the thermal compensation field 121.

The shimming effect is double. On one side the bars 120 located in the diagonals contribute to compensate magnetic field inhomogeneities produced by the remnant magnetic quadrupole moment; on the other side higher order moments are compensated by a second set of bars arranged in the directrix between the principal magnetic field bars array 110.

The geometrical arrangement and materials of magnetic bars 110 and 140 allow the thermal compensation effect on Bx. It is well known that the magnetization produced by magnetic materials generally present a negative thermal coefficient. Moreover, the same effect is produced by the thermal expansion of the bar array container. The basic principle consists of the generation the Bx field by the superposition of two fields of opposite direction, $Bx_1$ and $Bx_2$, each one formed by a plurality of properly arranged magnetic bars. The thermal coefficients of the magnetic bars with which are generated both fields have the same sign but substantially different values. Moreover, the magnetization generated in the center of the magnetic set for $Bx_1$ is substantially stronger than the one for $Bx_2$. For example, and without losing generality in the invention, the bars generating $Bx_1$ are chosen of an alloy of $Sm_2Co_{17}$ (temperature Coefficient $\alpha=-0.03\%/°$ C.) and the bars that generate $Bx_2$ are chosen of Ferrite 8 (Coefficient of temperature $\alpha=-0.20\%/°$ C.). Furthermore, if the temperature of the magnetic set increases, the diminution of the magnetization in the work zone 100 is produced by i) the diminution of the magnetization of the $Sm_2Co_{17}$ bars, and ii) by the thermal expansion of the packing disks of the bars array. As the magnetization produced respectively by $Sm_2Co_{17}$ and Ferrite 8 are opposite, and its thermal coefficient presents the same sign, the individual thermal changes in both magnetizations compensate the total internal magnetic field. Of course, in the calculation of the relative strength of $Bx_1$ and $Bx_2$ the thermal expansion of the packing discs must be taken into account.

Bx can be transversal or longitudinal to the flow direction. Further, and without losing the generality of the invention, we will refer to Bx indicating the magnetic field transversal to the flow direction in the fluid vein.

The device, which generates the homogeneous and thermally compensated magnetic field, is obtained by piling up a plurality of discs as described in FIG. 6, generally each one of different thickness. In addition, it is also possible to generate the spatially homogeneous magnetic field for this invention by an arrangement of magnetic bars of suitable length. To the practical effects, to obtain the best possible longitudinal homogeneity, and without supposing a loss in the generality of the invention, we refer further to the fact that the magnetic field of the measurement and characterization of the velocity profile device, is generated in the zone of interest 100 by a plurality of discs of variable thickness, piled up with variable separation between each other.

All the magnetic system is surrounded by a material of high magnetic permeability 180. By this media an increment in the concentration of magnetic flow lines is produced in the zone of interest and furthermore it contributes to obtain a better homogenization of the magnetic field in volume 100. This device contributes, in addition, to protect and to encapsulate the complete flow regime analytical system.

The system of magnetic bars used to generate the magnetic fields in application in Magnetic Resonance, arranged in discrete space positions, allows further constructing lighter embodiments than the conventional permanent magnets, allowing diminishing magnet construction costs, as well as in the mechanical movements of the device parts. It is further possible to interconnect electrical and/or electronic elements in the interstitial spaces between the magnetic bars, diminishing in this way the final volume and weight of the device.

Another embodiment consists in locating a plurality of magnetic bars 130, generating the spatial localization gradient 131, in another cylinder located in the external as well as internal part with regard to the main magnetic cylinder. Both cylinders, the gradient one and the principal magnetic one, can rotate the one with regard to the other, producing the suitable reorientation of the Gx gradient 131.

The fluid vein is introduced in a measurement and characterization set of the velocity profile by a non-magnetic tube 170 of arbitrary geometry, preferably of stainless steel, but with a radiofrequency transparent section, preferably made of a fiber glass tube approved by the oil industry, like the compound 316 SS. If the Bx field 111 is transversal, in this invention is preferably used a sole receiving/exciting coil of the solenoidal type 160. If another preferred embodiment is chosen, in which the magnetic field Bx 111 is longitudinal to the direction of the flow, the preferred receiving/exciting coil 160 is of the "birdcage" type. A skilled technician can design and construct these excitation and detection elements with the adapted bibliographic aid like for example: Jianming Jin, *Electromagnetic Analysis and Design in Resonant Magnetic Imaging*, pp. 193, CRC Press LLC (1999).

The grooved tube 150, constructed preferably in copper, contributes to the electromagnetic shield of the radio frequency system.

A not in the illustrated mechanical system figures, is in charge of rotating the set of measurement and characterization of the velocity profile in all the positions necessary to obtain the complex matrix of data, which can be possibly represented graphically in image form.

A non illustrated Magnetic Resonance hardware and software, which is either located in the proximity or away from the device of measurement and characterization of the velocity profile, but connected by signal reception and emission cables, is in charge of manipulating the radio frequency signals and the pertinent digital information.

Figure 7:
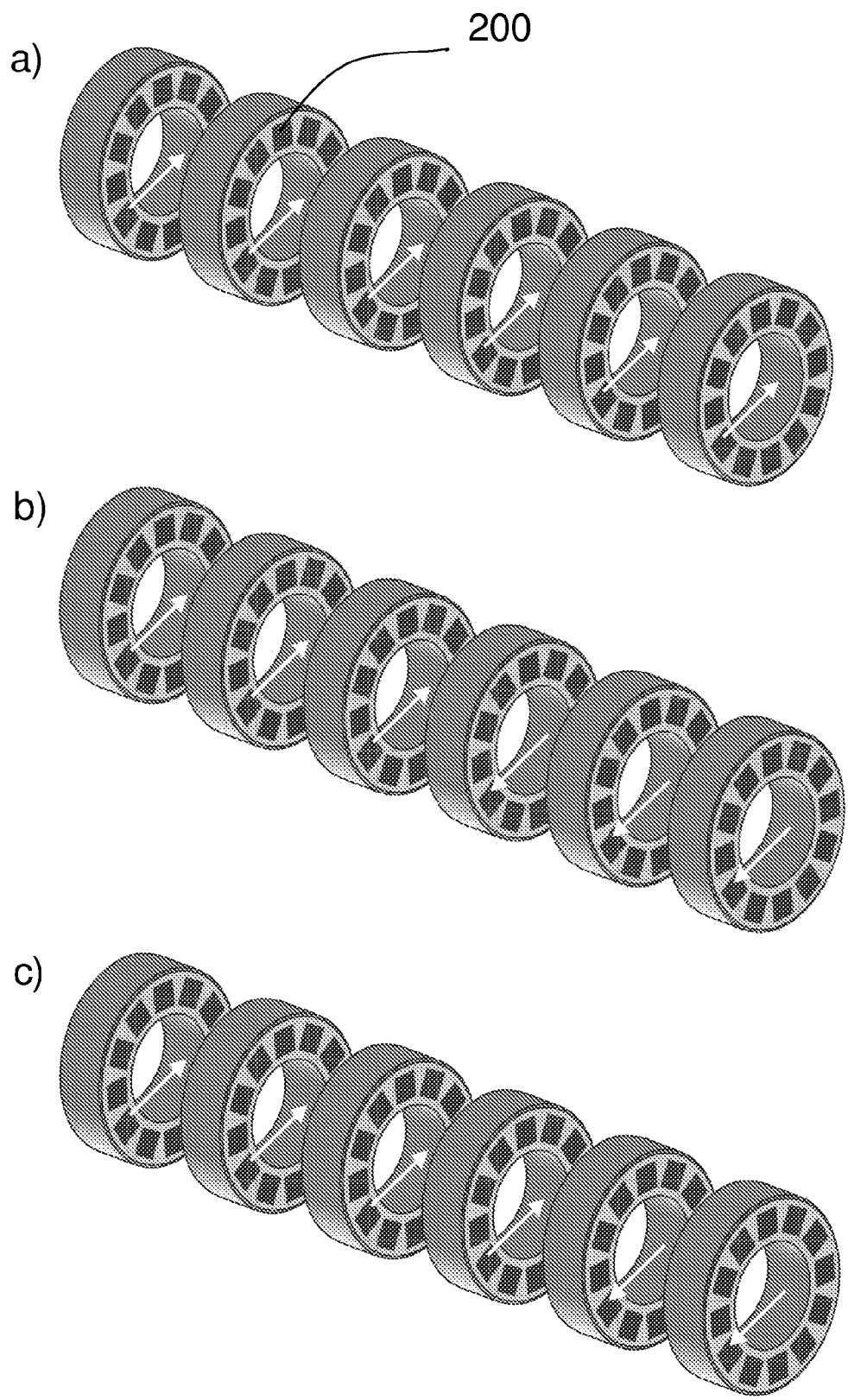
FIGS. 7a)-7c): Illustrate the preferred embodiment for the magnet of variable effective length for the prepolarization of the hydrogen nuclei of each component of the complex fluid.
Figure 8:
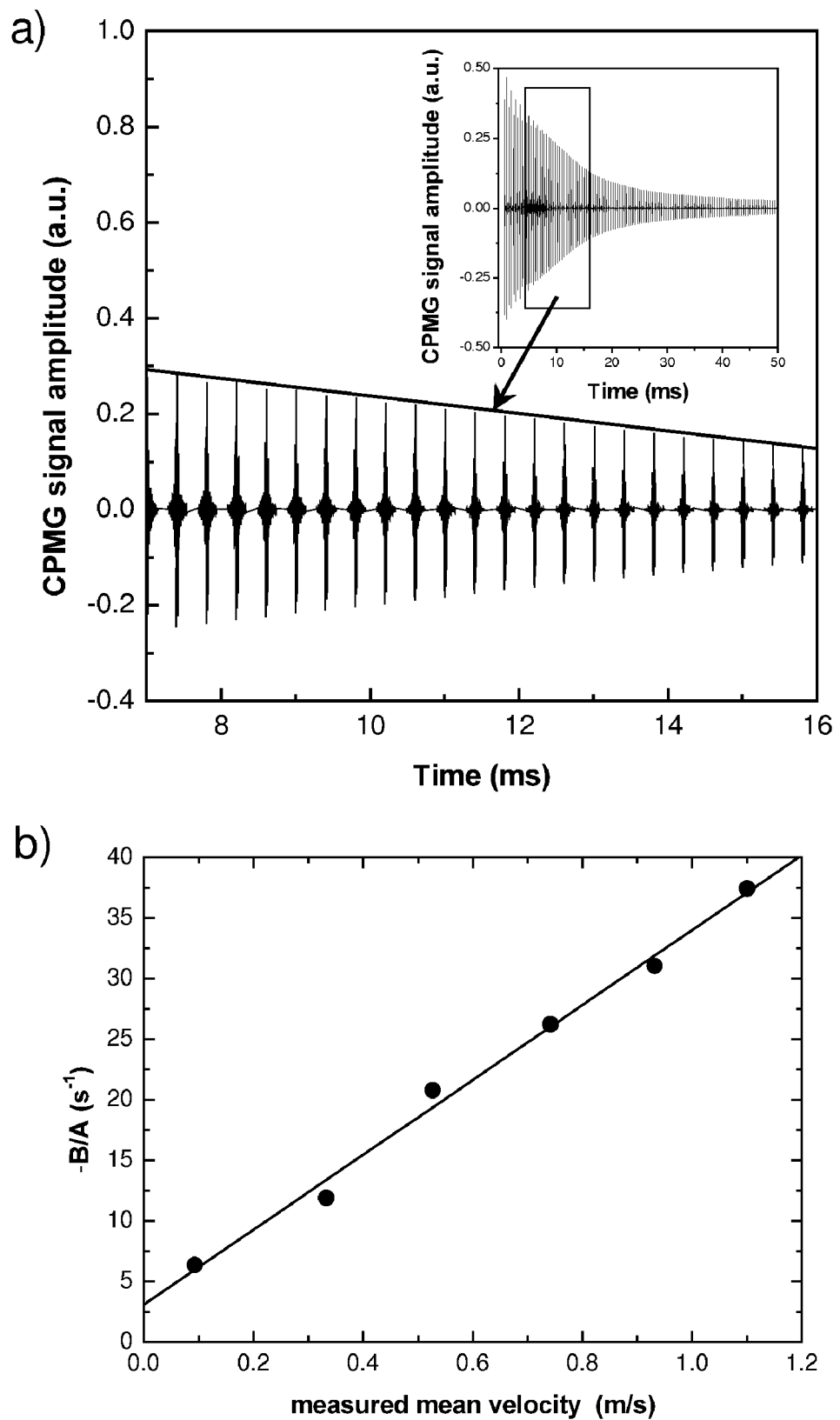
FIG. 8a) shows the succession of echoes that is obtained from the application of the CPMG sequence, for petroleum circulating at a velocity of 1.1 m/s; b) it shows the average fluid velocity of the –B/A ratio; where B is the slope and A is the y-axis interception at t=0 of the linear fit of CPMG echoes.

FIG. 7 illustrates a preferred embodiment for the magnet of variable effective length for the prepolarization of the hydrogen nuclei of each component of the complex fluid. The device is constituted by discrete Halbach-type magnetic discs (see FIG. 4) of variable thickness and separation 200, which can be rotated one with respect to the other by a not illustrated mechanical device. The effective polarization length of the magnet is determined by the relative number of discs whose internal fields are oriented in opposite directions. Obviously the maximum polarization length is reached when the individual magnetic fields of all the discs are oriented in the same direction, see FIG. 7 a). The array providing a prepolarization field of zero effective length is that where the discs are oriented with equal number in opposite directions, see FIG. 7 b). Finally, FIG. 7 c) illustrates an arrangement of discs that generates an effective polarization field of approximately one third of the maximum field. A medium skilled technician can design and construct this set in accordance to the expected symmetry of the measure velocity profile.

Measurements of average speed of the fluid and proportions of phases Methods: the preferred method for measuring the average velocity of the total flow, as well as the proportions of phases present in a multiphase fluid with at least two phases that produce a detectable MR signal, consists of using a pulse sequence known in the previous state-of-the-art like CPMG. The CPMG sequence is a sequence of pulses in the form $\pi/2 - \pi - \ldots - \pi$, in such a way that the magnetization that will be rotating on the x-y plane (detection plane) will be constructed with those portions of the sample that were originally excited by the first pulse of the sequence (the pulse of $\pi/2$) and that induces an electromotive force in the detection coil. We define the time origin of the sequence (t=0) at the moment at which the pulse $\pi/2$ starts to be applied. All the volume of the fluid inside the detection coil is excited during such a short time interval.

In order to produce a better understanding of the invention, without setting aside the general concept, the following analysis is restricted to the simplest case in which the fluid is composed by two phases, for example one of them is formation water and the other is petroleum or oil. In addition, in the present example, we will consider the case in which the production tube is completely filled with fluid during the measurement process (at least, the total volume of the pipe must be completely filled with fluid at the place where the MR sensor is located).

So, in t=0 the total volume of the fluid inside the MR sensor will be:

$$V_T(0) = V_A(0) + V_B(0) \quad (1)$$

where $V_A$ and $V_B$ represent the volume occupied by each one of the two phases present in the fluid.

If the fluid moves on at an average velocity v, the volume of sample that will produce a detectable MR signal at time t will be:

$$V_T(t) = V_T(0) - Svt \quad (2)$$

where S is the cross-section of the detection antenna.

At the time t, the following equations must be satisfied:

$$V_A(t) = V_A(0) - S_A vt = S_A(L - vt) \quad (3)$$

$$V_B(t) = V_B(0) - S_B vt = S_B(L - vt) \quad (4)$$

$$S_A + S_B = S, \quad (5)$$

where $S_A$ and $S_B$ represent the effective cross-sections inside the volume of the detection coil, corresponding to the phases A and B, respectively, and L represents the length of the detection coil.

Dividing the equation (3) by (4) we obtain:

$$\frac{V_A(t)}{V_B(t)} = \frac{S_A}{S_B} \quad (6)$$

The previous equation evaluated at time t=0 and at time t implies:

$$\frac{V_A(t)}{V_B(t)} = \frac{V_A(0)}{V_B(0)} \quad (7)$$

This means that, in the present approach, at any moment of time within the interval of duration of the CPMG sequence, the relative proportions of volumes of both phases are equal to they were at the moment t=0 when the pulse sequence began. So, the following expressions are easily deduced from the equations (3), (4) and (7):

$$V_A(t) = V_A(0)\left(1 - \frac{v}{L}t\right) \quad (8)$$

$$V_B(t) = V_B(0)\left(1 - \frac{v}{L}t\right) \quad (9)$$

On the other hand, the intensity of the CPMG signal at time t will be given by the following expression:

$$I(v, t) = I_A(v, t)e^{-\frac{t}{T_{2\it{eff}}^A}} + I_B(v, t)e^{-\frac{t}{T_{2\it{eff}}^B}} \quad (10)$$

where:

$$I_\alpha(v, t) = M_\alpha(v)V_\alpha(t) = f_\alpha(v)M_\alpha(0)V_\alpha(0)\left(1 - \frac{v}{L_{\it{eff}}}t\right) \quad (11)$$

In equation (10), v represents the average velocity of the flow and $T_{2\it{eff}}^\alpha$ represents the effective spin-spin relaxation time of the component $\alpha$. On the other hand, in equation (11), $M_\alpha(v)$ represents the magnetization per volume unit of the component $\alpha$ circulating at an average velocity v, $M_\alpha(0)$ represents the magnetization per volume unit of the component $\alpha$ at rest (v=0), $V_\alpha(0)$ is the volume of the component $\alpha$ inside the MR sensor at the beginning of the CPMG sequence (t=0), and $L_{\it{eff}}$ represents the effective length of the excitation/detection coil. The coefficient $f_\alpha(v)$ is called prepolarization factor and is given by:

$$f_\alpha(v) = \frac{M_\alpha(v)}{M_\alpha(0)} = \left(1 - e^{-\frac{L_{pol}}{vT_1^\alpha}}\right),$$

where $T_1^\alpha$ represents the longitudinal or spin-lattice relaxation time of the component $\alpha$, and $L_{pol}$ represents the length of the prepolarization stage, which means, the total length traveled by the fluid before entering to the MR sensor.

By the equation (11), the equation (10) can be written as follows:

$$I(v, t) = \left[M_A(0)f_A(0)V_A(0)e^{-\frac{t}{T_{2eff}^A}} + M_B(0)f_B(v)V_B(0)e^{-\frac{t}{T_{2eff}^B}}\right]\left(1 - \frac{v}{L_{eff}}t\right) \quad (12)$$

Of course, the expression (12) only has sense for those moments of the time t that satisfy $0 \leq 1(v/L)\, t \leq 1$.

Determination of the average speed of the fluid: An important observation of the equation (12) is that, for values of t that simultaneously satisfy the conditions $t/T^A_{2eff} \ll 1$ and $t/T^B_{2eff} \ll 1$, this expression is reduced to:

$$I(v, t) = [f_A(v)M_0^A V_A(0) + f_B(v)M_0^B V_B(0)]\left(1 - \frac{v}{L_{eff}}t\right) \quad (13)$$

The expression (13) shows that, if we make a fit of the amplitude of the echoes corresponding to the linear region of the CPMG sequence by an expression such as I(v,t)=A+B t, the quotient −B/A, between the slope and the y-axis intercept at t=0 of the fit, is directly proportional to the average velocity of the fluid being the proportionality constant equal to the reciprocal of the effective length of the excitation/detection antenna.

Determination of the fraction of components with prepolarization stage of fixed length (Method 1): The expression (13) shows that the y-axis intercept at t=0, obtained from the fit of the region where the intensity of the CPMG signal varies linearly for a given average velocity v of the fluid, determines the sum of the intensities due to the volume of each phase present in the fluid. In fact, these intensities are weighted with the polarization factors $f_\alpha(v)$ of each phase.

In general the exponentials present in the equation (13) can be approached by the first terms of their Taylor-series expansion which remarkably facilitates the fit of the expression (13) to the experimental data.

In the case where the circulating fluid is composed by two phases, by example petroleum and water, the y-axis intercept at t=0 of the fit of the CPMG sequence by the expression (13) will be given by the following expression:

$$I_0(v) = x_p I_p^0(v) + (1-x_p)I_w^0(v) \quad (14)$$

where $x_p$ represents the petroleum fraction, $I_p^0(v)$ and $I_w^0(v)$ represent, respectively, the y-intercept at t=0 for total content of petroleum and water, circulating at an average velocity v.

Regrouping terms in equation (14) we obtain:

$$I_0(v) = x_p\underbrace{(I_p^0(v) - I_w^0(v))}_{C(v)} + \underbrace{I_w^0(v)}_{D(v)} \quad (15)$$

$$I_0(v) = x_p C(v) + D(v)$$

Taking into account the expression (15) it can be seen that, for a given average velocity v of the fluid, there exists a linear relationship between the y-axis intercept at t=0 of the linear fit and the fraction of petroleum $x_p$ present in the fluid. So, if we carry out a fit of the experimental values of the y-axis intercepts at t=0 for different known petroleum concentrations $x_p$ by the expression (19), we can obtain the coefficients C(v) and D(v). Once the coefficients C(v) and D(v) are known, it is possible to obtain the value of an unknown petroleum concentration $x_p$ by the expression:

$$x_p = (I_0(v) - D(v))/C(v) \quad (16)$$

Determination of the fraction of components with prepolarization stage of variable length (Method 2): We define the coefficient $\gamma_\alpha(v)$ as the quotient of the prepolarization factors of the phase a circulating at an average velocity v, for two different lengths $L_1$ and $L_2$ of the prepolarization stage:

$$\gamma_\alpha(v) = \frac{f_\alpha(v, L_2)}{f_\alpha(v, L_1)} = \frac{\left(1 - e^{-\frac{L_2}{vT_1^\alpha}}\right)}{\left(1 - e^{-\frac{L_1}{vT_1^\alpha}}\right)} \quad (17)$$

Applying alternatively two CPMG sequences, one with a prepolarization stage of length $L_1$ and afterwards another one with a length $L_2$, we essentially have that the y-axis intercepts at t=0 of the linear fits of each pulse sequence satisfy the following equations:

$$I_{01}(v) = I_{p1}(v) + I_{w1}(v) \quad (18)$$

$$I_{02}(v) = I_{p2}(v) + I_{w2}(v) \quad (19)$$

In equation (19), $I_{p1}(v)$, $I_{w1}(v)$, $I_{p2}(v)$ and $I_{w2}(v)$ represent the contribution to the y-intercepts at t=0 of the linear fits of the CPMG signals corresponding to the contents of petroleum and water when a prepolarization stage of length $L_1$ y $L_2$ is used, respectively, for a fluid circulating at an average velocity v.

In addition, the following relationships must be satisfied:

$$\frac{I_{p2}}{I_{p1}} = \gamma_p(v) \quad (20)$$

$$\frac{I_{w2}}{I_{w1}} = \gamma_w(v) \quad (21)$$

Using the equations (18) and (19) and the equations (20) and (21) we easily find that the values of the unknown $I_{p1}$ e $I_{w1}$ values correspond to:

$$I_{p1}(v) = \frac{\gamma_w(v)I_{01}(v) - I_{02}(v)}{(\gamma_w(v) - \gamma_p(v))} \quad (22)$$

$$I_{w1}(v) = \frac{\gamma_p(v)I_{01}(v) - I_{02}(v)}{(\gamma_p(v) - \gamma_w(v))} \quad (23)$$

Knowing the calibration values $I^0_{p1}(v)$ and $I^0_{w1}(v)$, when each one of the phases separately is circulating at an average velocity v in a full conduit, we can calculate the absolute petroleum and formation water cuts circulating through the pipe, in the presence or, as well, in the absence of gas, air or a mixture of both.

What precedes, is referred to the method of measurement of the average velocity in a volume element of the production conduit, previously selected by the introduction of a magnetic field gradient which can be permanent or pulsed, and the selective irradiation of a volume inside the space bounded by the excitation antenna by a pulse of a narrow bandwidth—or "soft" pulse. In order to determine the flow regime in the production line, it is necessary to measure the velocity profile of the components of the fluid in the plane perpendicular to the direction of the flow, sweeping all the volume elements and applying a suitable method for data reduction to construct the image of the velocity profile on that plane. In the next, the measurement procedure is explained.

Figure 9:
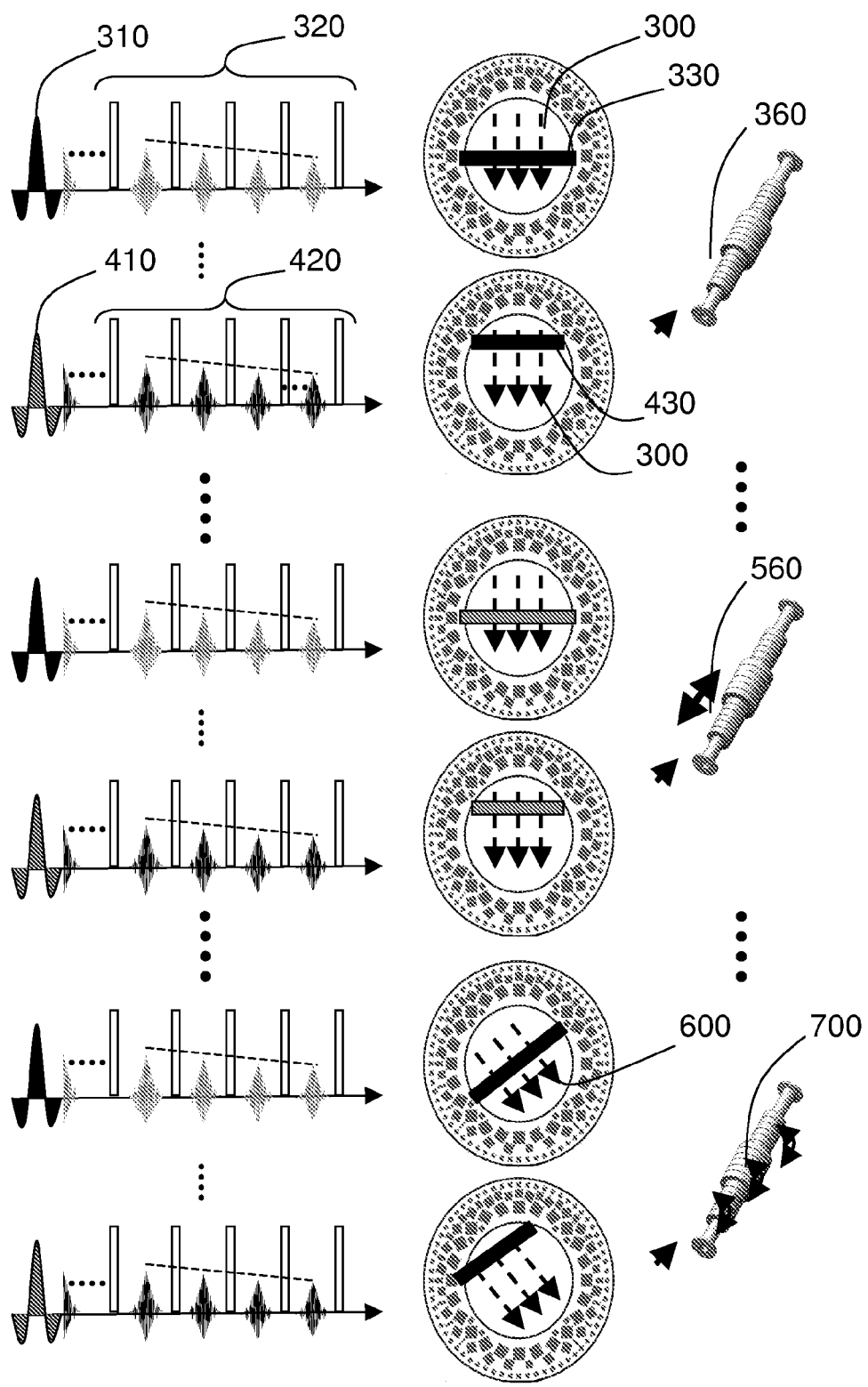
FIG. 9: Illustrates the MR measurement and analysis procedure to determine the transversal velocity profile and the relative proportions of the components of a complex fluid.

FIG. 9 shows the steps involved in the measurement sequence. The flow 350 enters into the analyzer set following a longitudinal direction and becomes polarized by the action of the second prepolarization field. Then, a selective excitation is performed to determine the velocity profile of each component of the fluid. The selective excitation is performed by the magnetic field gradient 300 along the plane which is transverse to the flow, and the excitation of the corresponding MR signals is accomplished by a first pulse frequency selective 310. The magnetic field gradient 300 must be confined essentially to the volume occupied by the radiofrequency antenna of the MR sensor and can be linear or radial with respect to that plane. The selective radiofrequency pulses of variable frequency 310, are modulated in amplitude and/or phase, preferably by a "sinc" function. After the application of the CPMG measurement sequence with space selection of the excitation 320, the velocity of the component of the fluid into the plane or slice 330, which has been excited by the first selective pulse 310 to a certain resonance frequency, is obtained. In the next step, it is selected another volume element 320 to be excited by means the pulse 310 keeping fixed the magnetic field gradient 300. The average velocity of the fluid inside this volume element is measured applying the preferred CPMG pulse sequence 320. These steps are repeated a suitable number of times for a fixed effective length of the prepolarization field 360. In the next step, the effective prepolarization length 360 is changed to the new value 560, and the previous procedure is repeated. All the procedure just described must be repeated the number of times necessary in order to obtain the data matrix needed to establish: i) The velocity profile projected along the magnetic field gradient axis 300, and ii) The relative fractions of each component of the fluid. Finally, in order to obtain a bi-dimensional velocity profile, the magnetic field gradient 300 is turned by a suitable angle, preferably turning all the analyzer set 700 and the previous sequences must be repeated. To obtain the bi-dimensional image of the velocity profile, is preferably adopted for this invention the simplest method known as "projection-reconstruction"; this method is described in: P. T. Callaghan, *"Principles of Nuclear Magnetic Resonance Microscopy"*, Clarendon Press, Oxford (1991).

A preferred embodiment refers to the determination of the velocity profile in a tube of cylindrical section. The magnetic field in the MR sensor module must have a radial field gradient into the transverse plane to the direction of the flow. The selective excitation will provide, for each preferred CPMG sequence of measurements, the average velocity in a transverse ring, whose radius will depend on the value of the magnetic field and the resonance frequency of excitation. This procedure is repeated for different values of the excitation frequency.

The procedure of measurement and analysis by magnetic resonance is performed by a conventional device: a transmitter Tx, with a plurality of filters, impedance matching and "blanking" circuits and a circuit to control the quality factor Q, a receiver Rx, with a plurality of reception channels and a plurality of filters, impedance matching and "blanking" circuits, a plurality of transmission/reception switches, a radiofrequency signals generator, preferably synthesized, a pulse generator, which provides a plurality of synchronized pulses of command, a device for digitizing the MR signal with a plurality of channels of reception/digitalization and a plurality of interfaces of connection to the control computer, to the measurement and analysis MR module and to the prepolarization module of variable length. A medium skilled technician in this matter can design and implement a measurement and analysis device of magnetic resonance for the present flow regime analyzer.

Where it is declared or described that a measurement pulse sequence is a CPMG it must be understood that this sequence is the preferred one for this invention. However, an alternative embodiment for this invention can be declared or described as any sequence for measuring the velocity profile of each component of the fluid which encodes or select an excitation volume element of certain antenna and, after that, another temporal pulse series of reading for measuring the time of permanence inside the MR sensor of the selected volume element be applied. In addition, it is declared that the pulse sequences known as SSFP and/or CPMG (described as an example in D. J. Pusiol, "Device and method for real time direct measurement of the proportion and flow-rate of a multi-component fluid", US 2006/0020403 A1; A. Abragam", *"The Principles of Nuclear Magnetism"*, Oxford University Press, 1973; y Bageira de Vazconcelos Azeredo R., Colnago A. L. and Engelsberg M., *Analytical Chemistry,* 72, 2401, 2000)), are another preferably measurement sequences.

Where it is declared or described that an apparatus of this invention includes, contains, posses, is compound or is constituted by certain components, it must be understood, except when this declaration or description expresses the contrary, that one or more of that or those explicitly described components can be present in the apparatus. Nevertheless, in an alternative embodiment, the apparatus of this invention can essentially be declared or described as consisting of certain components, in which the components of this embodiment could materially alter the operation principle or the differentiating characteristics of the apparatus, could not be present in the declaration or the description of this alternative embodiment. In another alternative embodiment, the apparatus of this invention can be declared or described as consisting of certain components, in which other components of the embodiment could not be declared or described.

Where the article "a" is used in a declaration of or in a description of the presence of a component in the apparatus of this invention, it must be understood, unless this declaration or description expresses explicitly the contrary, that the use of the indefinite article does not limit the presence of the component in the apparatus to one in number.

What we claim is:

1. A magnetic resonance based apparatus capable of measuring, without using time-of-flight measurements, flow regimes of multi-phase fluids in a pipe, comprising:
   a magnetic resonance module through which the fluid phases flow; and
   at least one pre-polarization module, said at least one pre-polarization module through which the fluid phases flow before entering the magnetic resonance module, wherein said pre-polarization module comprises a plurality of cylindrical segments that can be selectively combined so as to modify the effective length of the pre-polarization module, wherein each cylindrical segment comprises a Halbach-type magnet array.

2. The apparatus according to claim 1 wherein said at least one pre-polarization module includes a plurality of magnetic disks each comprising a Halbach-type magnet array, wherein said discs can be reoriented relative to each other so as to modify the effective polarization length to adjust the pre-polarization length to the particular the spin-lattice relaxation time of a selected phase of the multi-phase fluid.

3. The apparatus according to claim 1 wherein at least one pre-polarization module is positioned at each end of said magnetic resonance module such that, regardless of the direction of fluid flow in the pipe, fluid will flow through at least one pre-polarization module before entering the magnetic resonance module.

4. The apparatus according to claim 1 wherein said magnetic resonance module includes a Halbach-type magnet array.

5. The apparatus according to claim 4 wherein said magnetic resonance module generates an homogenous constant magnetic field that is thermally compensated using the addition of a space location gradient of discrete Halbach type.

6. The apparatus of claim 5 wherein said homogenization of said principal field is realized by a set of magnetic bars located in the diagonals with respect to the direction of said principal field, to compensate the quadrupole moment, and another set of said magnetic bars in the directrix between said bars generating said principal field to compensate multipolar contributions of major importance.

7. The apparatus according to claim 4 wherein at least one Halbach array comprises a plurality of magnetic bars of different sizes and materials, assembled in a plurality of discs that are stacked and interconnected.

8. The apparatus of claim 4 wherein thermal compensation is achieved in the magnetic resonance module by using at least two magnets having different magnetic susceptibility and thermal properties at different positions in the Halbach array.

9. The apparatus of claim 4 wherein the magnetic resonance module comprises at least two concentric cylinders of magnets around an axis and wherein the magnets in an radially outer cylinder are constructed of a different material than the magnets in a radially inner cylinder.

10. The apparatus of claim 8 wherein one cylinder is used to generate a homogenous and thermally compensated main magnetic field that is used to produce a magnetic resonance signal and the other cylinder is used to generate a magnetic field gradient.

11. The apparatus of claim 8 wherein both cylinders can rotate around the axis of the fluid conduit.

12. The apparatus of claim 1 wherein a plurality of digital radio frequency modules for magnetic resonance measurement are located remotely with respect to the flow line of the multiphase fluid.

* * * * *